United States Patent
Xu et al.

[11] Patent Number: 6,133,008
[45] Date of Patent: Oct. 17, 2000

[54] **METHOD FOR CLONING AND PRODUCING THE TFII RESTRICTION ENDONUCLEASE IN *E. COLI***

[75] Inventors: Shuang-yong Xu, Lexington; Pei-Chung Hsieh, Cambridge, both of Mass.

[73] Assignee: New England Biolabs, Inc., Beverly, Mass.

[21] Appl. No.: 09/306,881

[22] Filed: May 7, 1999

[51] Int. Cl.[7] .............................. C12N 9/22; C12N 15/55
[52] U.S. Cl. ................ 435/199; 435/320.1; 435/252.3; 536/23.2
[58] Field of Search ................... 495/199, 320.1, 495/252.3; 536/23.2

[56] References Cited

U.S. PATENT DOCUMENTS 5,498,535  3/1996  Fomenkov et al. .................. 435/172.3

OTHER PUBLICATIONS

Roberts, et al., Nucleic Acids Res. 26:338–350 (1998).
Kosykh, et al., Molec. Gen. Genet. 178:717–719 (1980).
Mann, et al., Gene 3:97–112 (1978).
Walder, et al., Proc. Nat. Acad. Sci. 78:1503–1507 (1981).
Bougueleret, et al., Nucl. Acid Res., 12:3659–3676 (1984).
Gingeras and Brooks, Proc. Natl. Acad. Sci. USA 80:402–406 (1983).
Theriault and Roy, Gene 19:355–359 (1985).
Blumenthal, et al., J. Bacteriol. 164:501–509 (1985).
Kiss, et al., Nucl. Acid Res. 13:6403–6421 (1985).
Szomolanyi, et al., Gene, 10:219–225 (1980).
Janulaitis, et al. Gene 20:197–204 (1982).
Kiss and Baldauf, Gene 21:111–119 (1983).
Walder, et al., J. Biol. Chem. 258:1235–1241 (1983).
Fomenkov, et al., Nucl. Acid Res. 223:2399–2403 (1994).

*Primary Examiner*—Charles Patterson, Jr.
*Attorney, Agent, or Firm*—Gregory D. Williams

[57] ABSTRACT

A genomic DNA library of *Thermus filiformis* was constructed using pBR322 as a cloning vector. The methylase selection method was used to clone the TfiI methylase gene (tfiIM). A clone carrying an active TfiI methylase was identified. After sequencing the complete TfiI methylase gene and its downstream DNA sequence, a recombinase homolog was found. Because the methylase and its cognate endonuclease gene are located in proximity to each other in a particular restriction-modification system, efforts were made to clone the upstream DNA by inverse PCR. After two rounds of inverse PCR, one open reading frame (ORF1) was found upstream of the TfiI methylase gene. This ORF1, containing a Shine-Dalgarno sequence and a TATA box on the upstream side, was cloned and expressed, and TfiI endonuclease activity was detected in crude cell extracts. It is concluded that ORF1 encodes TfiI restriction endonuclease.

7 Claims, 3 Drawing Sheets

FIG. 1

```
              10                  30                  50
ATGGGGCGAGCTCTGCACACCTACATAAAGTGGCCAGGTGGAAAGGGGCGGATCCTAAAG
 M  G  R  A  L  H  T  Y  I  K  W  P  G  G  K  G  R  I  L  K
              70                  90                 110
AAAATGGTTCCCCTTCTCCCAAGGGAAGTTTTTGATAAGGACTTCGTAGACCCCTTTTTT
 K  M  V  P  L  L  P  R  E  V  F  D  K  D  F  V  D  P  F  F
             130                 150                 170
GGGGGGGGCTCTTCCCTGCTAGCCTTTAGGCCCAAGAGGAAAGCCTTTATAAGCGATATA
 G  G  G  S  S  L  L  A  F  R  P  K  R  K  A  F  I  S  D  I
             190                 210                 230
GATCCCGATTTAATGACTTTCTATGCTTTGGTTTCCGAAAAGAACCACGATCTTTTGGAT
 D  P  D  L  M  T  F  Y  A  L  V  S  E  K  N  H  D  L  L  D
             250                 270                 290
TATATCTTTTCCTTAAGCAAATTCTGGGATCAGTTTGACTACTTCGTGTCCTATACGGTA
 Y  I  F  S  L  S  K  F  W  D  Q  F  D  Y  F  V  S  Y  T  V
             310                 330                 350
GATTGGGATAACGGAGCTATTGAAAATTTGAAGATAGAGGTACCAAGCGAGCCTATCCAA
 D  W  D  N  G  A  I  E  N  L  K  I  E  V  P  S  E  P  I  Q
             370                 390                 410
AAATACAAAGAAGAGCTCACCATACATATAGGAAGGAGCATTAACCAAAAGCTGAAGAAA
 K  Y  K  E  E  L  T  I  H  I  G  R  S  I  N  Q  K  L  K  K
             430                 450                 470
TTAAGATCCATTTTGGCTAGAGCATATGAGGAAAGGGGAAACAAGCTGGACGAAGCAGCG
 L  R  S  I  L  A  R  A  Y  E  E  R  G  N  K  L  D  E  A  A
             490                 510                 530
AGAAAAACTCACGTAGAAACAGCAGCTAGGGGGGGCTTTTACTATTTCTTAAGAGACATT
 R  K  T  H  V  E  T  A  A  R  G  G  F  Y  Y  F  L  R  D  I
             550                 570                 590
TTCAACAAAGAAATAACTGCTGAAGACCCTCTCAGGTATGCAGCATTCTACTTCGTGAGG
 F  N  K  E  I  T  A  E  D  P  L  R  Y  A  A  F  Y  F  V  R
             610                 630                 650
GAGCTATGCTTTGGCTCCATGTTCCGATTCAATGACCTTGGAAAGTTCAATATCCCTTAT
 E  L  C  F  G  S  M  F  R  F  N  D  L  G  K  F  N  I  P  Y
             670                 690                 710
GGAGGAATGTCTTACAACGGCAAGAGGTTTAATGAAAAACTTAAAACGATTATTCACGGT
 G  G  M  S  Y  N  G  K  R  F  N  E  K  L  K  T  I  I  H  G
             730                 750                 770
AATCCAGGCGAACTGCTGAGACATTCCACTATCAGGGTGGCAGACTTTCGAGAAACCCTC
 N  P  G  E  L  L  R  H  S  T  I  R  V  A  D  F  R  E  T  L
             790                 810                 830
AAGGACGTTGGCAGAGGTTACTTCGTTTTTTTAGACCCTCCTTACCTGACCGACTTTTCC
 K  D  V  G  R  G  Y  F  V  F  L  D  P  P  Y  L  T  D  F  S
             850                 870                 890
GAATATGGAGGCTATAGCTTCACAGAAAAAGATCACATGGATTTGATCGACTGGTTGGAG
 E  Y  G  G  Y  S  F  T  E  K  D  H  M  D  L  I  D  W  L  E
             910                 930                 950
GATTTTGACGGAGATTACTTGCTTATAGTTGCAGGCAAAAAAACCGTAAGCCTTTACGAG
 D  F  D  G  D  Y  L  L  I  V  A  G  K  K  T  V  S  L  Y  E
             970                 990                1010
AAAAAGCTGAGGATGATGAAGAAAGGTTTCATTTATACCTTCGACGGAGAGTTTAGATTT
 K  K  L  R  M  M  K  K  G  F  I  Y  T  F  D  G  E  F  R  F
            1030                1050                1070
TCCGTTAGGAACAGAAACGAAAGAGAGACTAGGTACCTCATTGCAACCTCAAAGTCCTTA
 S  V  R  N  R  N  E  R  E  T  R  Y  L  I  A  T  S  K  S  L
            1090                1110
AACCGGGAACACCTTATGATAGCATACCCCCTTTTTTCAGAGTGA
 N  R  E  H  L  M  I  A  Y  P  L  F  S  E  *
```

FIG. 2

```
           10                  30                  50
ATGAGTGCCAAAGAAAGCGCACCTGAAAAATTTGTTTTGGATAGCTATATTGAACACCTG
 M  S  A  K  E  S  A  P  E  K  F  V  L  D  S  Y  I  E  H  L
           70                  90                 110
AAAGAACATTTTCAAGCAGCTCTCTCCGAAACGAAGAGTTCCGTGGAAAACAACCTCAGG
 K  E  H  F  Q  A  A  L  S  E  T  K  S  S  V  E  N  N  L  R
          130                 150                 170
AAAAACCTGGAGAATAAGCGGAAGCAATGGCCTTACAGCTTGCTCCTTGGGGAGAGAGAG
 K  N  L  E  N  K  R  K  Q  W  P  Y  S  L  L  L  G  E  R  E
          190                 210                 230
CTCCGATATTTGACGATCACTAGTTCCCTTGAGTCAAAGCTAGGCAGTTCATTGGAAAAA
 L  R  Y  L  T  I  T  S  S  L  E  S  K  L  G  S  S  L  E  K
          250                 270                 290
GCAATAAGGGATTTCGTTAAGAGGCATTTGGCTCATTGGCAAGTGCCAGAAGAGTCGGGT
 A  I  R  D  F  V  K  R  H  L  A  H  W  Q  V  P  E  E  S  G
          310                 330                 350
AAAAAGGGGTCGGGTAGAAAGAAGAAGCCTGATTTGGTGATTATAGACACGGAAGGCGAG
 K  K  G  S  G  R  K  K  K  P  D  L  V  I  I  D  T  E  G  E
          370                 390                 410
AGGAAAACCGTTTATGTTTTTGAGCTGAAAGTTGGCGGAAATATGGATAATACCAAAATA
 R  K  T  V  Y  V  F  E  L  K  V  G  G  N  M  D  N  T  K  I
          430                 450                 470
CCCGGGGAGATTAGTAAACTGAAGAATGTGGCGAATAATGTAAGGCAAGAAATTACAGAC
 P  G  E  I  S  K  L  K  N  V  A  N  N  V  R  Q  E  I  T  D
          490                 510                 530
TGCCAAAACCTGGAGGCTTATTTGGCTATTTTGGTAGATGATCAAACGGTAGTAAGCAGA
 C  Q  N  L  E  A  Y  L  A  I  L  V  D  D  Q  T  V  V  S  R
          550                 570                 590
ATAAAGAACTCGGCTTCTTCAGAAGGTGTAAAAGTTATAGGAGGTAGGGAGTTTTGGGGG
 I  K  N  S  A  S  S  E  G  V  K  V  I  G  G  R  E  F  W  G
          610                 630                 650
ATGCTTTTCAGCGTGAAGGACAATGGGATGTTAGACTATGTGGAAGAAAAAGTGAAGGAT
 M  L  F  S  V  K  D  N  G  M  L  D  Y  V  E  E  K  V  K  D
          670                 690                 710
GCTTATAAAAGAGCTGCGCAAGAGGTTAAATTCTCAAACTTATTTGAACCAAATCCCTAA
 A  Y  K  R  A  A  Q  E  V  K  F  S  N  L  F  E  P  N  P  *
```

FIG. 3

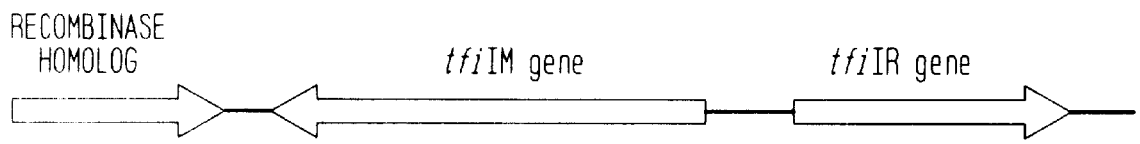

METHOD FOR CLONING AND PRODUCING THE TFII RESTRICTION ENDONUCLEASE IN E. COLI

BACKGROUND OF THE INVENTION

The present invention relates to recombinant DNA which encodes the TfiI restriction endonuclease as well as TfiI methylase, and the production of TfiI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and thirty restriction endonucleases with unique specificities have been identified among the many hundreds of bacterial species that have been examined to date (Roberts and Macelis, *Nucl. Acids Res.* 24:223–235, (1996)).

Restriction endonucleases typically are named according to the bacteria from which they are derived. Thus, the species *Deinococcus radiophilus* for example, produces three different restriction endonucleases, named DRaI, DRaII and DRaIII. These enzymes recognize and cleave the sequences 5'TTTAAA3', 5'PuGGNCCPy3' and 5'CACNNNGTG3'respectively. *Escherichia coli* RY13, on the other hand, produces only one enzyme, EcoRI, which recognizes the sequence 5'GAATTC3'.

A second component of bacterial restriction-modification (R-M) systems are the methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., Mol. Gen. Genet. 178: 717–719, (1980); HhaII: Mann et al., Gene 3: 97–112, (1978); PstI: Walder et al., Proc. Nat. Acad. Sci. 78: 1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acids. Res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985)).

A third approach, and one that is being used to clone a growing number of R-M systems are now being cloned by selection for an active methylase gene (U.S. Pat. No. 5,200, 333 and BsuRI: Kiss et al., Nucl. Acids. Res. 13: 6403–6421, (1985)). Since R-M genes are often closely linked, both genes can often be cloned simultaneously. This selection does not always yield a complete restriction system however, but instead yields only the methylase gene (BspRI: Szomolanyi et al., Gene 10: 219–225, (1980); BcnI: Janulaitis et al., Gene 20: 197–204 (1982); BsuRI: Kiss and Baldauf, Gene 21: 111–119, (1983); and MspI: Walder et al., J. Biol. Chem. 258: 1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535, (1996); Fomenkov et al., Nucl. Acids Res. 22:2399–2403, (1994)). This method utilizes the *E. coli* SOS response following DNA damages caused by restriction endonucleases or non-specific nucleases. A number of thermostable nuclease genes (Tth111I, BsoBI, Tf nuclease) have been cloned by this method.

Because purified restriction endonucleases, and to a lesser extent, modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

The methylase selection method was used to clone the TfiI methylase gene (tfiIM) from *Thermus filiformis* genome. An active TfiI methylase was cloned in *E. coli* using an expression vector pBR322. After cloning the complete TfiI methylase gene and its downstream DNA sequences, a recombinase homolog was found downstream of the TfiI methylase. Because methylase gene and restriction endonuclease gene are located in proximity to each other in a particular restriction-modification system, efforts were made to clone the upstream DNA by inverse PCR. After two rounds of inverse PCR reactions one open reading frame (ORFs) was found upstream of the TfiI methylase gene. Expression of the first open reading frame (ORF1) in a T7 expression vector yielded partially active TfiI endonuclease.

Cells containing the pACYC184-TfiIM and pAII17-TfiIR plasmids are unstable in large cultures. To improve the stability of the cells, we introduced another plasmid, pSX20-T7lys carrying the T7 lysozyme gene to reduce the activity of T7 RNA polymerase, into the expression system. Cells containing these three plasmids produce $1\times10^5$ units of TfiI endonuclease per gram of wet E. coli cells following IPTG induction. DNA sequencing indicated that this TfiI endonulease contains 12 amino acid deletion at the N-terminus. This deletion variant was designated as TfiI-s. It was assumed that the protein translation started from a TTG codon.

To clone the full-length tfiIR gene (ORF1), the gene was amplified by PCR, digested with NdeI and BamHI, gel-purified, cloned into NdeI and BamHI cut and CIP treated pACYC184-T7ter. The ligated plasmid was transformed into ER2566 [pBR322-TfiIM] cells. Cell extracts prepared from IPTG-induced cells ER2566 [pBR322-TfiIM, pACYC184-T7ter-TfiIR] displayed TfiI endonuclease activity. Sequencing analysis among the active clones shows a full-length tfiIR gene (ORF1) has been obtained. To improve basal expression level of TfiI endonuclease, a compatible plasmid pSX20-T7lys was introduced into the above cells. Cells carried three plasmids [pSX20-T7lys, pBR322-TfiIM, pACYC184-T7ter-TfiIR] were grown on a LB plate containing Ampicillin (100 μg/ml), chloramphenicol (33 μg/ml) and kanamycin (50 μg/ml). From these clones, TfiI endonuclease was expressed at 20,000–50,000 units per gram of wet E. coli cells after IPTG-induction.

BRIEF DESCRIPTION OF THE DRAWINGS

FIG. 1 TfiI methylase gene (SEQ ID NO:1) and its encoded amino acid sequence (SEQ ID NO:2).

FIG. 2 TfiI endonuclease gene (SEQ ID NO:3) and its encoded amino acid sequence (SEQ ID NO:4).

FIG. 3 Gene organization of TfiI restriction-modification system.

DETAILED DESCRIPTION OF THE INVENTION

Figure 4:
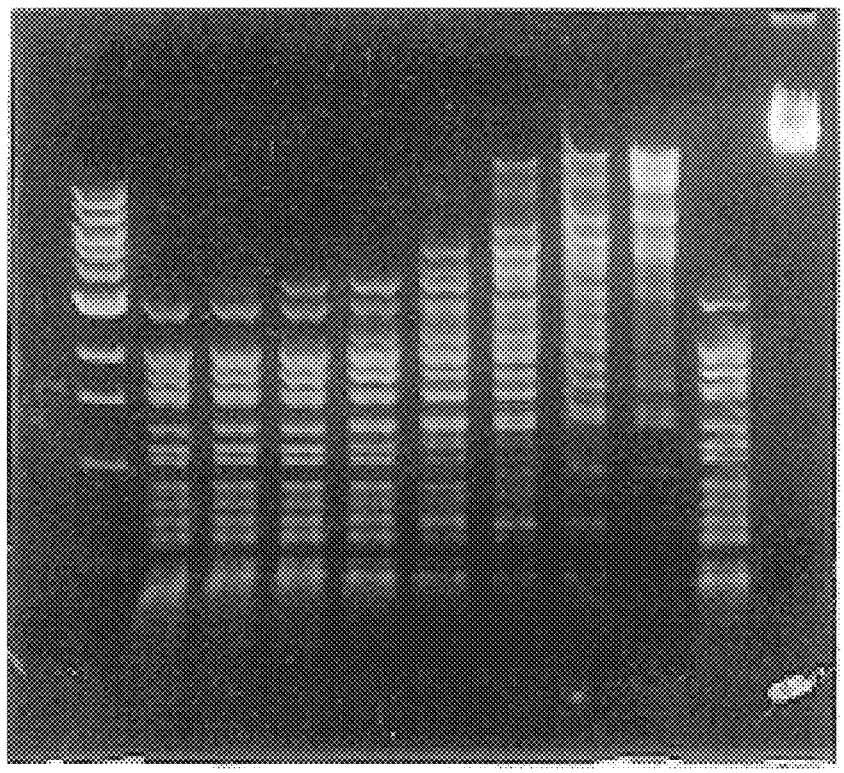
FIG. 4 TfiI endonuclease activity assay in cell extract. Lane 1, DNA size marker; Lanes 2 to 9, serial delution of cell extract containing recombinant TfiI; lane 10, purified (native) TfiI control; lane 11, uncut λDNA.

The method described herein by which the TfiI methylase gene and the TfiI restriction endonuclease genes are preferably cloned and expressed in E. coli using the following steps:
1. Construction of a Sau3AI partial genomic DNA library.

*Thermus filiformis* genomic DNA was digested with Sau3AI to achieve the desired partial digestion. The Sau3AI partially digested genomic DNA was ligated into BamHI cut and CIP treated vector pBR322 at 16° C. overnight. Electroporation was carried out using RR1 competent cells and ligated DNA. The transformants were pooled and amplified. Plasmid DNA was prepared from the overnight cell cultures.
2. Challenge the Sau3AI partial library DNA with TfiI digestion and cloning of TfiI methylase gene.

The Sau3AI partial library DNA was digested with TfiI at 65° C. overnight. The digested DNA was used to re-transform RR1 competent cells. Plasmid DNA was isolated from cell culture of all transformants. Individual plasmid DNA was digested with TfiI to detect any resistance to digestion. Only one plasmid isolate #18 displayed resistance to TfiI digestion.
3. Cloning and sequencing of the insert carrying the TfiI methylase gene.

Two HindIII-digested fragments and two KpnI-digested fragments derived from the original insert were gel-purified and subcloned in pUC19. The isolate #18 plasmid DNA were sequenced using pBR322 BamHI site primer (NEB#1219) while the HindIII, and KpnI subclones were sequenced using pUC19 forward and reverse primers. Sequence homology search indicated that the KpnI-digested fragment (around 719 bp) is highly homologous to known N6-adenine methylase, suggesting that it is part of the TfiI methylase gene. To sequence the remaining portion of the TfiI methylase, a primer walking method was employed. The tfiIM gene is 1122 bp, encoding a protein with 374 aa. The coding sequence and the predicted aa sequence is shown in FIG. 1. The rest of the new DNA downstream of the TfiI methylase gene encodes a recombinase homolog. An ATG start codon was found in the upstream of the newly derived sequence. To confirm the junction sequence around the Sau3A site, an inverse PCR method was adopted. Inverse PCR products were found in self-ligated DNA of BfaI and HpaII cleaved DNA. Inverse PCR products were gel-purified from PCR reactions of BfaI and HpaII cleaved and self-ligated DNA. The inverse PCR products were sequenced. Four hundred and fifty base pairs of new sequence were derived from DNA sequencing of BfaI and HpaII inverse PCR products, which is consistent with the TfiI methylase sequence from clone #18. Since restriction-modification genes are located in proximity to each other, it was reasoned that the TfiI endonuclease gene is likely to be located upstream of the methylase gene.
4. Cloning of TfiI restriction endonuclease gene.

Inverse PCR was carried out to clone the genomic DNA upstream of the TfiI methylase gene. Inverse PCR products were obtained from NlaIII and HhaI cut and self-ligated template DNA. The DNA fragment was gel-purified and sequenced. The newly derived DNA sequence extended out further ~1000 bp. Translation of those DNA sequence upstream of the TfiI methylase in six reading frames indicated that there is only one open reading frame (ORF1) with minimum 200 amino acids. This gene is transcribed in the direction as opposed to the TfiI methylase gene. The tfiIR gene is 717 bp, encoding a protein with 239 aa. The coding sequence and the predicted aa sequence is shown in FIG. 2. The gene organization of TfiI R-M system is shown in FIG. 3.
5. Expression of TfiI methylase gene in E. coli.

The entire TfiI methylase gene (1125 bp) was amplified from genomic DNA using Vent® DNA polymerase and two primers in PCR. The PCR product (TfiI methylase gene) was digested with SphI, gel-purified and cloned into pACYC184 and pBR322 plasmid. Both plasmids with TfiIM gene insertion displayed full resistance to TfiI digestion, indicating modification of TfiI sites in vivo via the insertion and expression of the TfiI methylase gene. The TfiI methylase (374 aa, molecular mass=44 kDa) is homologous to most of the known N6-adenine methylases.
6. Expression of tfiIR gene (ORF1) in T7 expression vector, pAII17.

PCR was carried out to amplify tfiIR (ORF1) gene. The PCR product was digested with NdeI and BamHI and gel-purified. The tfiIR gene (ORF1) was cloned into NdeI and BamHI cut and CIP treated pAII17. Sixteen out of thirty-six pAII17-derivative plasmids with insert were isolated. Cell extracts, prepared from IPTG-induced cells ER2566 [pACYC184-TfiIM, pAII17-TfiIR], were used to assay for TfiI endonuclease activity. The assay showed that four clones carried partial TfiI endonuclease activity, while the remaining 12 clones did not show any enzymatic activity. DNA sequencing analysis on the active clones showed that a point mutation was introduced, resulting in a frame shift in tfiIR gene (ORF1). This mutation might account for the low TfiI activity observed in the cell extracts. In addition, this result also suggests that the TfiI endonuclease might be toxic in vivo. In order to reduce the expression level of TfiI protein, we introduced a compatible plasmid pSX20-T7lys, which expresses the T7 lysozyme to reduce the $T_7$ RNA polymerase activity. Cells carried three plasmids [pSX20-T7Lys, pACYC184-TfiIM, pAII17-TfiR] were selected on a LB plate containing ampicillin (100 μg/ml), chloramphenicol (33 μg/ml) and kanamycin (50 μg/ml). Two out of seven clones were found containing TfiI endonuclease activity (100,000 units/g of wet cells). Sequence analysis indicated that translation of TfiI endonuclease starts from a TTG start codon, the number 13th codon of the full-length tfiR gene. The ATG codon was deleted in these two clones. We named this TfiI endonuclease variant as TfiI-s (s for short). TfiI-s has 12 aa deletion at the N-terminus, but still displays TfiI activity.

7. Expression of full-length TfiI (27.1 kDa) in a T7 expression vector pACYC184-$T_7$ter.

In order to clone the full-length tfiIR gene (ORF1), the gene was amplified by PCR, digested with NdeI and BamHI and gel-purified. The tfiIR gene (ORF1) DNA fragment was cloned into NdeI and BamHI cut and CIP treated pACYC184-$T_7$ter. Fourteen out of eighteen pACYC184-$T_7$ter-derivative plasmids with insert were isolated. Cell extracts, prepared from IPTG-induced cells ER2566 [pBR322-TfiIM, pACYC184-$T_7$ter-TfiIR], were used to assay TfiI endonuclease activity. The assay showed that four clones displayed partial TfiI endonuclease activity, while the remaining 14 clones did not show any enzymatic activity. The non-active clones probably contain mutations in the tfiIR gene (ORF1). Sequencing analysis among the active clones shows that the full-length tfiIR gene (ORF1) has been obtained. To reduce the basal expression level of TfiI endonuclease, we also introduced a plasmid pSX20-T7lys, as described above, into the cells. Cells carrying three plasmids [pSX20-T7lys, pBR322-TfiIM, pACYC184-$T_7$ter-TfiIR] were grown on a LB plate containing ampicillin (100 μg/ml), chloramphenicol (33 μg/ml) and kanamycin (50 μg/ml). From these clones, we were able to produce TfiI endonuclease about 20,000–50,000 units per gram of wet *E. coli* cells after IPTG-induction.

The present invention is further illustrated in the following Example. This Example is provided to aid in the understanding of the invention and is not construed as a limitation thereof.

The references cited above and below are herein incorporated by reference.

EXAMPLE 1

Cloning of TfiI Restriction-Modification System in *E.coli*

Genomic DNA was prepared from *Thermus filiformis* (New England Biolabs' collection, NEB #570, Cowan et al, unpublished result).

1. Construction of a Sau3AI partial genomic DNA library

Five μg of *Thermus filiformis* genomic DNA was digested with 2, 1, 0.5, 0.25 and 0.125 units of Sau3AI at 37° C. for 30 min. 0.5 and 0.25 units of digestion gave rise to the desired partial digestion. The purified partially-digested genomic DNA was ligated into BamHI cut and CIP treated vector pBR322 at 16° C. overnight. Transformation was carried out by mixing RR1 (TonA⁻, DnaseI⁻) competent cells and the ligated DNA by electroporation. Electroporation was carried out using electro-competent RR1 (TonA⁻, DnaseI⁻) cells and ligated DNA. About 50,000 transformants were obtained. All the transformants were pooled and inoculated into 1 liter of LB broth plus Amp and incubated at 37° C. overnight. Plasmid DNA was prepared from the overnight cells by Qiagen maxi columns.

2. Challenge the Sau3AI partial library DNA with TfiI digestion and cloning of TfiI methylase gene 0.5 and 5 μg of the Sau3AI partial library DNA was digested with 20 units of TfiI at 65° C. for 5 hours. The digested DNA was used to re-transform ER2502 competent cells. Thirty-one transformants were obtained. Mini-preparation of plasmid DNA was isolated from 2 ml cell culture of each 18 transformants. Individual plasmid DNA was digested with TfiI to detect any resistance to digestion. One plasmid isolate #18 displayed resistance to TfiI digestion. Restriction digestion of #18 plasmid DNA with BamHI, EcoRI, KpnI, HindIII, SalI, and SphI indicated that it contains an insert of approximately 4.5 kb DNA.

3. Subcloning and sequencing of the insert carrying the TfiI methylase gene

The clone #18 plasmid DNA was digested with KpnI, HindIII, and BamHI respectively. Two EcoRI fragments, two HindIII fragments and four BamHI fragments derived from the insert were gel-purified and subcloned in pUC19. The original isolate #18 plasmid DNA and all the EcoRI, HindIII, and NdeI subclones were sequenced using pUC19 forward and reverse primers or pBR322 primers (NEB#1219, NEB#1208, NEB#1245 and NEB#1223). The DNA sequence of KpnI-degested fragment (~710 bp) was found to be homologous to known N6 adenine methylases when it was compared to the known gene in GenBank using Blastx program search. To sequence the remaining portion of the TfiI methylase, a primer (202-191) was synthesized to walk toward to the C-terminal region of the methylase.

5' TCATTTATACCTTCGACGGAGAGT 3'
(202-191) (SEQ ID NO:5)

Additional 400 bps were identified. Among the new sequences, 110 bps were found to be the C-terminus of the TfiI methylase, and the remaining sequences is homologous to known recombinases.

To sequence the N-terminal portion of the TfiI methylase, a primer (202-192) was synthesized to walk toward the N-terminus of the TfiI methylase gene.

5' TTGGTTAATGCTCCTTCCTATATG 3'
(202-192) (SEQ ID NO:6)

Additional 500 bps were identified. Among these new sequences, 430 bps were found to be the N-terminal coding region of the TfiI methylase. Since there is a BamHI site in the sequences, we confirm the flanking sequences around the BamHI site by inverse PCR. *Thermus filiformis* genomic DNA was cleaved with AflII, BbvCI, BfaI, HpaII, KpnI, NcoI, NdeI, NheI, PstI and RsaI. The restriction enzyme cleaved DNA was self-ligated at a low concentration (2 μg/ml) and the self-ligated circular molecules were used as templates in inverse PCR using a set of primers:

5° CTCCCAAGGGAAGTTTTTGATAAGG 3'
(203-168) (SEQ ID NO:7)

5' AAGGGGAACCATTTTCTTTAGGATC 3'
(203-169) (SEQ ID NO:8)

Inverse PCR conditions 95° C. 1' 55° C. 1', 72° C. 2', for 30 cycles were employed. Inverse PCR products were found in self-ligated DNA of BfaI and HpaII cleaved DNA. Inverse PCR products were gel-purified. DNA sequencing was performed using primer 202-192, 203-168 and 203-169. The sequence obtained from inverse PCR is consistent with that obtained from #18 clone, indicating that the flanking sequences around BamHI are correct. A complete open reading frame, consisted of 1122 bp (374 aa, 44 kDa), was identified, and sequence alignment analysis indicated that this ORF is an N6-adenine methylase. Hence, we designated this ORF as TfiI methylase gene (tfiIM). Since restriction-modification genes are located in proximity to each other, it was reasoned that the TfiI endonuclease gene is likely to be located upstream of the methylase gene.

4. Cloning of TfiI restriction endonuclease gene

Inverse PCR was carried out to clone the genomic DNA upstream of the TfiI methylase gene. A set of inverse PCR primers were made based on the upstream of TfiI methylase gene. *Thermus filiformis* genomic DNA was cleaved with ApoI, EaeI, EcoRI, HhaI, MscI, MseI, NlaIII, and TaqI respectively. The digested DNA was self-ligated at a low concentration (2 µg/ml) and the circular molecules were used as templates in inverse PCR using a set of primers:

5' CAGGAAAAACCTGGAGAATAAGCGG 3'
(203-170) (SEQ ID NO:9)

5' AGGTTGTTTTCCACGGAACTCTTCG 3'
(203-171) (SEQ ID NO:10)

Inverse PCR was performed at 95° C. 1', 55° C. 1', 72° C. 2'for 30 cycles using primers 203-170 and 203-171.

Inverse PCR products were found in self-ligated DNA of ApoI, HhaI, MscI, MseI, and NlaIII cleaved DNA. Inverse PCR products 0.4 kb and 1 lb were gel-purified from PCR reactions of HhaI and NlaIII cleaved and self-ligated DNA, respectively. DNA sequencing was performed using primer 203-170 and 203-171. Four hundred base pairs of sequence was derived from DNA sequencing of HhaI and NlaIII inverse PCR products. To sequence the remaining region of the NlaIII inverse PCR product, three primers were synthesized.

5' GTAGATGATCAAACGGTAGTAAGC 3'
(204-149) (SEQ ID NO:11)

5' ATGGGATGTTAGACTATGTGGAAG 3'
(204-150) (SEQ ID NO:12)

5' GAGGAGATCGCCTCCCAGGAGACC 3'
(204-151) (SEQ ID NO:13)

The newly derived DNA sequence extended out further 520 bp. A 717 bp open reading frame was observed in the inverse PCR product, and we tentitively designated this gene as tfiIR gene (ORF1).

5. Expression of TfiI methylase gene in *E. coli*

The entire TfiI methylase gene (1122 bp) was amplified from genomic DNA using Vent® DNA polymerase and two primers in PCR (95° C. 1', 58° C. 1', 72° C. 3', for 20 cycles). The two primers have the following sequences:

5' ATGCAGCATGCGGAGGAATAATA-
CATGGGGCGAGCTCTGCACACCTAC 3'
(203-174) (SEQ ID NO:14)

5' CTGCATGCATGCTCACTCTGAAAAAAGGGGGTATGCT 3'
(203-178) (SEQ ID NO:15)

The PCR product (tfiIM gene) was digested with SphI, gel-purified and cloned into pACYC184 and pBR322. Six pACYC184-derivative plasmids containing the methylase gene insert were digested with TfiI. Only one isolate displayed full resistance to TfiI digestion. Nine pBR322-derivative plasmids containing the methylase gene insert were digested with TfiI. Only one isolate displayed full resistance to TfiI digestion. Nevertheless, these two clones are indicative of modification of TfiI sites in vivo via the insertion and expression of the TfiI methylase gene. The TfiI methylase (374 aa, molecular mass=44 kDa) also carries the conserved N6-adenine methylase motifs based on the information from the Blastp program. It was concluded that the 1122 bp DNA encodes TfiI methylase activity.

6. Expression of tfiIR gene (ORF1) in T7 expression vector pAII17 plasmid.

Expression vector pAII17 is a modified pET11 T7 expression vector that contains four copies of transcription terminators upstream of T7 promoter (Kong et al. J. Biol. Chem. 268:1965–1975 (1993)). Two primers were synthesized for PCR amplification of tfiIR gene (ORF1):

5' GGAGAGTTACATATGAGTGCCAAAGAAAGCGCACCTG 3'
(205-74) (SEQ ID NO:16)

5' GTGCATGGATCCTTAGGGATTTGGT-
TCAAATAAGTTTGAG 3' (205-75). (SEQ ID NO:17)

PCR was carried out using Vent® DNA polymerase, primers 205-74 and 205-75 under conditions of 95° C. 1', 60° C. 1', 72° C. 1', for 20 cycles. The PCR product was digested with NdeI and BamHI at 37° C. overnight, gel-purified and the resulting DNA was cloned into NdeI and BamHI cut pAII17 expression vector. ER2566 [pACYC184-TfiIM, pAII17-TfiIR] cells were induced with IPTG. Cell lysates were prepared and assayed for TfiI endonuclease activity using λ DNA as a substrate. Upon the induction of IPTG, the cells became sick and formed aggregations at the bottom of tubes. Four out of eighteen clones showed very partial activity. Sequence results of these four clones indicates that a point mutation occurred in the ORF resulting in a frame shift. This suggests that the TfiI endonuclease is toxic in vivo in spite of the methylation protection from TfiI methylase. In order to stabilize the cells, we introduced a compatible plasmid pSX20-T7lys in addition to pACYC184-TfiIM and pAII17-TfiIR into ER2566 strain. Two out of seven clones were found to have TfiI endonuclease activity (100,000 units/gram of wet cells). However, sequencing results indicated that the TfiI endonuclease gene from these two clones lacks the first 12 amino acids at N-terminus. The shortened TfiI is presumed to start translation at the TTG start codon. We named the short derivative as TfiI-s.

7. Expression of tfiIR gene (ORF1) in T7 expression vector pACYC184-T7ter plasmid.

To express the full-length tfiIR gene (ORF1), a low copy number T7 expression vector (pACYC184-T7ter) was constructed. First, the EagI-HindIII fragment of pACYC184 was replaced by the EagI -HindIII fragment from pET11d that carries the T7 promoter and transcription terminator to yield plasmid, pACYC184-T7. Second, the SphI-BamHI fragment of pACYC184-T7 was replaced by SphI-BamHI fragment of pAII17 to yield plasmid, pACYC184-T7ter. The NdeI and BamHI site downstream of T7 promoter was used for cloning DNA. TfiI endonuclease gene was amplified by PCR as described previously and the DNA fragment was cloned into NdeI/BamHI cut and CIP treated pACYC-T7ter. Thirteen plasmids out of eighteen colonies with insert were isolated. Cell extracts were prepared from IPTG-induced cells ER2566 [pBR322-TfiIM, pACYC-T7ter-TfiIR]. Only four clones carrying partial TfiI endonuclease activity were detected. Similar to the situation of cells with pACYC184-TfiIM and pAII17-TfiIR, the cells became sick and got precipitated at the bottom of tubes upon IPTG induction.

Therefore, we introduced a compatible plasmid pSX20-T7lys to the cells and then examined TfiI endonuclease activity.

ER2566 [pBR322-TfiIM, pACYC184-T7ter-TfiIR, pSX20-T7lys] cells were grown in 10 ml LB+Amp (100 μg/ml)+Cm (33 μg/ml)+Km (50 μg/ml) to late log phase and induced by addition of IPTG (final 0.5 mM concentration) for 3.5 h at 30° C. The induced cells were harvested and resuspended in 1 ml sonication buffer (10 mM Tris-HCl, pH 8, 1 mM EDTA). Cells were lysed by sonication. Following centrifugation to remove all debris, cell extract was assayed on λ DNA substrates for TfiI endonuclease activity at 65° C. for 1 h. Two cell extracts (#31 and #34) displayed TfiI endonuclease activity. These two cells also displayed TfiI endonuclease activity in cell extracts prepared from 500 ml of IPGT-induced cells. The enzyme activity yield is about 2–5×10$^4$ units/gram of wet *E. coli* cells (IPTG-induced). DNA sequencing results indicated that the full-length tfiIR gene (ORF1) was obtained.

The strain ER2566 [pBR322-TfiIM, pACYC184-T7ter-TfiIR, pSX20-T7lys], NEB#1197, has been deposited under the terms and conditions of the Budapest Treaty with the American Type Culture Collection on May 7, 1999 and received ATCC Accession No. PTA-29.

What is claimed is:

1. Isolated DNA coding for the TfiI restriction endonuclease, wherein the isolated DNA is obtainable from *Thermus filiformis*.

2. A recombinant DNA vector comprising a vector into which a DNA segment encoding the TfiI restriction endonuclease has been inserted.

3. Isolated DNA encoding the TfiI restriction endonuclease and methylase, wherein the isolated DNA is obtainable from ATCC No. PTA-29.

4. Isolated DNA encoding a 12-amino acid deletion variant of TfiI restriction endonuclease.

5. A cloning vector which comprises the isolated DNA of claim 3 or 4.

6. A host cell transformed by the vector of claim 2 or 5.

7. A method of producing TfiI restriction endonuclease comprising culturing a host cell transformed with the vector of claim 2 or 5 under conditions suitable for expression of said endonuclease.

* * * * *

UNITED STATES PATENT AND TRADEMARK OFFICE
CERTIFICATE OF CORRECTION

PATENT NO. : 6,133,008
DATED : October 17, 2000
INVENTOR(S) : Shuang-yong Xu and Pei-Chung Hsieh It is certified that error appears in the above-identified patent and that said Letters Patent is hereby corrected as shown below:

```
Column 2, line 16     replace "Acids." with --Acids--
Column 2, line 24     replace "Acids." with --Acids--
Column 2, line 39     replace "damages" with --damage--
Column 3, line 23     replace "a" with --an--
Column 5, line 8      replace "a" with --an--
Column 5, line 39     replace "a" with --an--
Column 6, line 29     replace "degested" with --digested--
Column 6, line 34     after "toward" delete "to"
Column 6, line 40     replace "is" with --are--
Column 7, line 49     replace "tentitively" with
                      --tentatively--
```

Signed and Sealed this

Eighth Day of May, 2001

Attest:

NICHOLAS P. GODICI

Attesting Officer    Acting Director of the United States Patent and Trademark Office

SEQUENCE LISTING

<160> NUMBER OF SEQ ID NOS: 17

<210> SEQ ID NO 1
<211> LENGTH: 1125
<212> TYPE: DNA
<213> ORGANISM: Thermus filiformis
<220> FEATURE:
<221> NAME/KEY: CDS
<222> LOCATION: (1)..(1122)

<400> SEQUENCE: 1

```
atg ggg cga gct ctg cac acc tac ata aag tgg cca ggt gga aag ggg      48
Met Gly Arg Ala Leu His Thr Tyr Ile Lys Trp Pro Gly Gly Lys Gly
 1               5                  10                  15 cgg atc cta aag aaa atg gtt ccc ctt ctc cca agg gaa gtt ttt gat      96
Arg Ile Leu Lys Lys Met Val Pro Leu Leu Pro Arg Glu Val Phe Asp
            20                  25                  30 aag gac ttc gta gac ccc ttt ttt ggg ggg ggc tct tcc ctg cta gcc     144
Lys Asp Phe Val Asp Pro Phe Phe Gly Gly Gly Ser Ser Leu Leu Ala
        35                  40                  45 ttt agg ccc aag agg aaa gcc ttt ata agc gat ata gat ccc gat tta     192
Phe Arg Pro Lys Arg Lys Ala Phe Ile Ser Asp Ile Asp Pro Asp Leu
    50                  55                  60 atg act ttc tat gct ttg gtt tcc gaa aag aac cac gat ctt ttg gat     240
Met Thr Phe Tyr Ala Leu Val Ser Glu Lys Asn His Asp Leu Leu Asp
65                  70                  75                  80 tat atc ttt tcc tta agc aaa ttc tgg gat cag ttt gac tac ttc gtg     288
Tyr Ile Phe Ser Leu Ser Lys Phe Trp Asp Gln Phe Asp Tyr Phe Val
                85                  90                  95 tcc tat acg gta gat tgg gat aac gga gct att gaa aat ttg aag ata     336
Ser Tyr Thr Val Asp Trp Asp Asn Gly Ala Ile Glu Asn Leu Lys Ile
            100                 105                 110 gag gta cca agc gag cct atc caa aaa tac aaa gaa gag ctc acc ata     384
Glu Val Pro Ser Glu Pro Ile Gln Lys Tyr Lys Glu Glu Leu Thr Ile
        115                 120                 125 cat ata gga agg agc att aac caa aag ctg aag aaa tta aga tcc att     432
His Ile Gly Arg Ser Ile Asn Gln Lys Leu Lys Lys Leu Arg Ser Ile
    130                 135                 140 ttg gct aga gca tat gag gaa agg gga aac aag ctg gac gaa gca gcg     480
Leu Ala Arg Ala Tyr Glu Glu Arg Gly Asn Lys Leu Asp Glu Ala Ala
145                 150                 155                 160 aga aaa act cac gta gaa aca gca gct agg ggg ggc ttt tac tat ttc     528
Arg Lys Thr His Val Glu Thr Ala Ala Arg Gly Gly Phe Tyr Tyr Phe
                165                 170                 175 tta aga gac att ttc aac aaa gaa ata act gct gaa gac cct ctc agg     576
Leu Arg Asp Ile Phe Asn Lys Glu Ile Thr Ala Glu Asp Pro Leu Arg
            180                 185                 190
```

| | | |
|---|---|---|
| tat gca gca ttc tac ttc gtg agg gag cta tgc ttt ggc tcc atg ttc<br>Tyr Ala Ala Phe Tyr Phe Val Arg Glu Leu Cys Phe Gly Ser Met Phe<br>195 200 205 | | 624 |
| cga ttc aat gac ctt gga aag ttc aat atc cct tat gga gga atg tct<br>Arg Phe Asn Asp Leu Gly Lys Phe Asn Ile Pro Tyr Gly Gly Met Ser<br>210 215 220 | | 672 |
| tac aac ggc aag agg ttt aat gaa aaa ctt aaa acg att att cac ggt<br>Tyr Asn Gly Lys Arg Phe Asn Glu Lys Leu Lys Thr Ile Ile His Gly<br>225 230 235 240 | | 720 |
| aat cca ggc gaa ctg ctg aga cat tcc act atc agg gtg gca gac ttt<br>Asn Pro Gly Glu Leu Leu Arg His Ser Thr Ile Arg Val Ala Asp Phe<br>245 250 255 | | 768 |
| cga gaa acc ctc aag gac gtt ggc aga ggt tac ttc gtt ttt tta gac<br>Arg Glu Thr Leu Lys Asp Val Gly Arg Gly Tyr Phe Val Phe Leu Asp<br>260 265 270 | | 816 |
| cct cct tac ctg acc gac ttt tcc gaa tat gga ggc tat agc ttc aca<br>Pro Pro Tyr Leu Thr Asp Phe Ser Glu Tyr Gly Gly Tyr Ser Phe Thr<br>275 280 285 | | 864 |
| gaa aaa gat cac atg gat ttg atc gac tgg ttg gag gat ttt gac gga<br>Glu Lys Asp His Met Asp Leu Ile Asp Trp Leu Glu Asp Phe Asp Gly<br>290 295 300 | | 912 |
| gat tac ttg ctt ata gtt gca ggc aaa aaa acc gta agc ctt tac gag<br>Asp Tyr Leu Leu Ile Val Ala Gly Lys Lys Thr Val Ser Leu Tyr Glu<br>305 310 315 320 | | 960 |
| aaa aag ctg agg atg atg aag aaa ggt ttc att tat acc ttc gac gga<br>Lys Lys Leu Arg Met Met Lys Lys Gly Phe Ile Tyr Thr Phe Asp Gly<br>325 330 335 | | 1008 |
| gag ttt aga ttt tcc gtt agg aac aga aac gaa aga gag act agg tac<br>Glu Phe Arg Phe Ser Val Arg Asn Arg Asn Glu Arg Glu Thr Arg Tyr<br>340 345 350 | | 1056 |
| ctc att gca acc tca aag tcc tta aac cgg gaa cac ctt atg ata gca<br>Leu Ile Ala Thr Ser Lys Ser Leu Asn Arg Glu His Leu Met Ile Ala<br>355 360 365 | | 1104 |
| tac ccc ctt ttt tca gag tga<br>Tyr Pro Leu Phe Ser Glu<br>370 | | 1125 |

<210> SEQ ID NO 2
<211> LENGTH: 374
<212> TYPE: PRT
<213> ORGANISM: Thermus filiformis

<400> SEQUENCE: 2

Met Gly Arg Ala Leu His Thr Tyr Ile Lys Trp Pro Gly Gly Lys Gly
 1               5                  10                  15

Arg Ile Leu Lys Lys Met Val Pro Leu Leu Pro Arg Glu Val Phe Asp
            20                  25                  30

Lys Asp Phe Val Asp Pro Phe Gly Gly Gly Ser Ser Leu Leu Ala
        35                  40                  45

Phe Arg Pro Lys Arg Lys Ala Phe Ile Ser Asp Ile Asp Pro Asp Leu
    50                  55                  60

Met Thr Phe Tyr Ala Leu Val Ser Glu Lys Asn His Asp Leu Leu Asp
65                  70                  75                  80

Tyr Ile Phe Ser Leu Ser Lys Phe Trp Asp Gln Phe Asp Tyr Phe Val
                85                  90                  95

Ser Tyr Thr Val Asp Trp Asp Asn Gly Ala Ile Glu Asn Leu Lys Ile
            100                 105                 110

Glu Val Pro Ser Glu Pro Ile Gln Lys Tyr Lys Glu Glu Leu Thr Ile
        115                 120                 125

```
His Ile Gly Arg Ser Ile Asn Gln Lys Leu Lys Leu Arg Ser Ile
    130                 135                 140

Leu Ala Arg Ala Tyr Glu Glu Arg Gly Asn Lys Leu Asp Glu Ala Ala
145                 150                 155                 160

Arg Lys Thr His Val Glu Thr Ala Ala Arg Gly Gly Phe Tyr Tyr Phe
                165                 170                 175

Leu Arg Asp Ile Phe Asn Lys Glu Ile Thr Ala Glu Asp Pro Leu Arg
                180                 185                 190

Tyr Ala Ala Phe Tyr Phe Val Arg Glu Leu Cys Phe Gly Ser Met Phe
                195                 200                 205

Arg Phe Asn Asp Leu Gly Lys Phe Asn Ile Pro Tyr Gly Gly Met Ser
    210                 215                 220

Tyr Asn Gly Lys Arg Phe Asn Glu Lys Leu Lys Thr Ile Ile His Gly
225                 230                 235                 240

Asn Pro Gly Glu Leu Leu Arg His Ser Thr Ile Arg Val Ala Asp Phe
                245                 250                 255

Arg Glu Thr Leu Lys Asp Val Gly Arg Gly Tyr Phe Val Phe Leu Asp
                260                 265                 270

Pro Pro Tyr Leu Thr Asp Phe Ser Glu Tyr Gly Gly Tyr Ser Phe Thr
                275                 280                 285

Glu Lys Asp His Met Asp Leu Ile Asp Trp Leu Glu Asp Phe Asp Gly
    290                 295                 300

Asp Tyr Leu Leu Ile Val Ala Gly Lys Lys Thr Val Ser Leu Tyr Glu
305                 310                 315                 320

Lys Lys Leu Arg Met Met Lys Lys Gly Phe Ile Tyr Thr Phe Asp Gly
                325                 330                 335

Glu Phe Arg Phe Ser Val Arg Asn Arg Asn Glu Arg Glu Thr Arg Tyr
                340                 345                 350

Leu Ile Ala Thr Ser Lys Ser Leu Asn Arg Glu His Leu Met Ile Ala
                355                 360                 365

Tyr Pro Leu Phe Ser Glu
        370

<210> SEQ ID NO 3
<211> LENGTH: 720
<212> TYPE: DNA
<213> ORGANISM: Thermus filiformis
<220> FEATURE:
<221> NAME/KEY: CDS
<222> LOCATION: (1)..(717)

<400> SEQUENCE: 3 atg agt gcc aaa gaa agc gca cct gaa aaa ttt gtt ttg gat agc tat      48
Met Ser Ala Lys Glu Ser Ala Pro Glu Lys Phe Val Leu Asp Ser Tyr
 1               5                  10                  15 att gaa cac ctg aaa gaa cat ttt caa gca gct ctc tcc gaa acg aag      96
Ile Glu His Leu Lys Glu His Phe Gln Ala Ala Leu Ser Glu Thr Lys
                20                  25                  30 agt tcc gtg gaa aac aac ctc agg aaa aac ctg gag aat aag cgg aag     144
Ser Ser Val Glu Asn Asn Leu Arg Lys Asn Leu Glu Asn Lys Arg Lys
            35                  40                  45 caa tgg cct tac agc ttg ctc ctt ggg gag aga gag ctc cga tat ttg     192
Gln Trp Pro Tyr Ser Leu Leu Leu Gly Glu Arg Glu Leu Arg Tyr Leu
        50                  55                  60 acg atc act agt tcc ctt gag tca aag cta ggc agt tca ttg gaa aaa     240
Thr Ile Thr Ser Ser Leu Glu Ser Lys Leu Gly Ser Ser Leu Glu Lys
65                  70                  75                  80
```

| | |
|---|---|
| gca ata agg gat ttc gtt aag agg cat ttg gct cat tgg caa gtg cca<br>Ala Ile Arg Asp Phe Val Lys Arg His Leu Ala His Trp Gln Val Pro<br>                85                    90                  95 | 288 |
| gaa gag tcg ggt aaa aag ggg tcg ggt aga aag aag aag cct gat ttg<br>Glu Glu Ser Gly Lys Lys Gly Ser Gly Arg Lys Lys Lys Pro Asp Leu<br>              100                 105                110 | 336 |
| gtg att ata gac acg gaa ggc gag agg aaa acc gtt tat gtt ttt gag<br>Val Ile Ile Asp Thr Glu Gly Glu Arg Lys Thr Val Tyr Val Phe Glu<br>            115                 120                125 | 384 |
| ctg aaa gtt ggc gga aat atg gat aat acc aaa ata ccc ggg gag att<br>Leu Lys Val Gly Gly Asn Met Asp Asn Thr Lys Ile Pro Gly Glu Ile<br>130                     135                 140 | 432 |
| agt aaa ctg aag aat gtg gcg aat aat gta agg caa gaa att aca gac<br>Ser Lys Leu Lys Asn Val Ala Asn Asn Val Arg Gln Glu Ile Thr Asp<br>145                   150                 155                160 | 480 |
| tgc caa aac ctg gag gct tat ttg gct att ttg gta gat gat caa acg<br>Cys Gln Asn Leu Glu Ala Tyr Leu Ala Ile Leu Val Asp Asp Gln Thr<br>                 165                 170                175 | 528 |
| gta gta agc aga ata aag aac tcg gct tct tca gaa ggt gta aaa gtt<br>Val Val Ser Arg Ile Lys Asn Ser Ala Ser Ser Glu Gly Val Lys Val<br>            180                 185                190 | 576 |
| ata gga ggt agg gag ttt tgg ggg atg ctt ttc agc gtg aag gac aat<br>Ile Gly Gly Arg Glu Phe Trp Gly Met Leu Phe Ser Val Lys Asp Asn<br>                195                 200                205 | 624 |
| ggg atg tta gac tat gtg gaa gaa aaa gtg aag gat gct tat aaa aga<br>Gly Met Leu Asp Tyr Val Glu Glu Lys Val Lys Asp Ala Tyr Lys Arg<br>210                     215                 220 | 672 |
| gct gcg caa gag gtt aaa ttc tca aac tta ttt gaa cca aat ccc taa<br>Ala Ala Gln Glu Val Lys Phe Ser Asn Leu Phe Glu Pro Asn Pro<br>225                   230                 235 | 720 |

<210> SEQ ID NO 4
<211> LENGTH: 239
<212> TYPE: PRT
<213> ORGANISM: Thermus filiformis

<400> SEQUENCE: 4

Met Ser Ala Lys Glu Ser Ala Pro Glu Lys Phe Val Leu Asp Ser Tyr
1               5                   10                  15

Ile Glu His Leu Lys Glu His Phe Gln Ala Ala Leu Ser Glu Thr Lys
            20                  25                  30

Ser Ser Val Glu Asn Asn Leu Arg Lys Asn Leu Glu Asn Lys Arg Lys
        35                  40                  45

Gln Trp Pro Tyr Ser Leu Leu Leu Gly Glu Arg Glu Leu Arg Tyr Leu
    50                  55                  60

Thr Ile Thr Ser Ser Leu Glu Ser Lys Leu Gly Ser Ser Leu Glu Lys
65                  70                  75                  80

Ala Ile Arg Asp Phe Val Lys Arg His Leu Ala His Trp Gln Val Pro
                85                  90                  95

Glu Glu Ser Gly Lys Lys Gly Ser Gly Arg Lys Lys Lys Pro Asp Leu
            100                 105                 110

Val Ile Ile Asp Thr Glu Gly Glu Arg Lys Thr Val Tyr Val Phe Glu
        115                 120                 125

Leu Lys Val Gly Gly Asn Met Asp Asn Thr Lys Ile Pro Gly Glu Ile
    130                 135                 140

Ser Lys Leu Lys Asn Val Ala Asn Asn Val Arg Gln Glu Ile Thr Asp
145                 150                 155                 160

-continued

```
Cys Gln Asn Leu Glu Ala Tyr Leu Ala Ile Leu Val Asp Asp Gln Thr
                165                 170                 175

Val Val Ser Arg Ile Lys Asn Ser Ala Ser Ser Glu Gly Val Lys Val
            180                 185                 190

Ile Gly Gly Arg Glu Phe Trp Gly Met Leu Phe Ser Val Lys Asp Asn
        195                 200                 205

Gly Met Leu Asp Tyr Val Glu Glu Lys Val Lys Asp Ala Tyr Lys Arg
    210                 215                 220

Ala Ala Gln Glu Val Lys Phe Ser Asn Leu Phe Glu Pro Asn Pro
225                 230                 235
```

<210> SEQ ID NO 5
<211> LENGTH: 24
<212> TYPE: DNA
<213> ORGANISM: Synthetic
<400> SEQUENCE: 5
tcatttatac cttcgacgga gagt                                           24

<210> SEQ ID NO 6
<211> LENGTH: 24
<212> TYPE: DNA
<213> ORGANISM: Synthetic
<400> SEQUENCE: 6
ttggttaatg ctccttccta tatg                                           24

<210> SEQ ID NO 7
<211> LENGTH: 24
<212> TYPE: DNA
<213> ORGANISM: Synthetic
<400> SEQUENCE: 7
ctcccaaggg aagtttttga taag                                           24

<210> SEQ ID NO 8
<211> LENGTH: 24
<212> TYPE: DNA
<213> ORGANISM: Synthetic
<400> SEQUENCE: 8 aagggaacc attttcttta ggat                                            24

<210> SEQ ID NO 9
<211> LENGTH: 25
<212> TYPE: DNA
<213> ORGANISM: Synthetic
<400> SEQUENCE: 9
caggaaaaac ctggagaata agcgg                                          25

<210> SEQ ID NO 10
<211> LENGTH: 25
<212> TYPE: DNA
<213> ORGANISM: Synthetic
<400> SEQUENCE: 10
aggttgtttt ccacggaact cttcg                                          25

<210> SEQ ID NO 11
<211> LENGTH: 24
<212> TYPE: DNA

-continued

```
<213> ORGANISM: Synthetic

<400> SEQUENCE: 11
gtagatgatc aaacggtagt aagc                                              24

<210> SEQ ID NO 12
<211> LENGTH: 24
<212> TYPE: DNA
<213> ORGANISM: Synthetic

<400> SEQUENCE: 12
atgggatgtt agactatgtg gaac                                              24

<210> SEQ ID NO 13
<211> LENGTH: 24
<212> TYPE: DNA
<213> ORGANISM: Synthetic

<400> SEQUENCE: 13
gaggagatcg cctcccagga gacc                                              24

<210> SEQ ID NO 14
<211> LENGTH: 39
<212> TYPE: DNA
<213> ORGANISM: Synthetic

<400> SEQUENCE: 14
atgcagcatg cggaggaata atacatgggg cgagctctg                              39

<210> SEQ ID NO 15
<211> LENGTH: 37
<212> TYPE: DNA
<213> ORGANISM: Synthetic

<400> SEQUENCE: 15
ctgcatgcat gctcactctg aaaaaagggg gtatgct                                37

<210> SEQ ID NO 16
<211> LENGTH: 37
<212> TYPE: DNA
<213> ORGANISM: Synthetic

<400> SEQUENCE: 16
ggagagttac atatgagtgc caaagaaagc gcacctg                                37

<210> SEQ ID NO 17
<211> LENGTH: 39
<212> TYPE: DNA
<213> ORGANISM: Synthetic

<400> SEQUENCE: 17
gtgcatggat ccttagggat ttggttcaaa taagtttga                              39
```